(12) United States Patent
Park et al.

(10) Patent No.: US 7,744,936 B2
(45) Date of Patent: Jun. 29, 2010

(54) METHOD FOR PREPARING EXTRACT FROM WILD GINSENG SHOWING ANTICANCER ACTIVITY AND THE COMPOSITION COMPRISING THE SAME

(75) Inventors: Yong Jin Park, Daejeon (KR); In Sop Shim, Cyeonggi-do (KR); Gyu Yong Song, Daejeon (KR)

(73) Assignee: Seocksanteo Medical Co., Ltd., Daejeon (KR)

( * ) Notice: Subject to any disclaimer, the term of this patent is extended or adjusted under 35 U.S.C. 154(b) by 303 days.

(21) Appl. No.: 11/572,131

(22) PCT Filed: Aug. 2, 2004

(86) PCT No.: PCT/KR2004/001941

§ 371 (c)(1),
(2), (4) Date: Jan. 15, 2007

(87) PCT Pub. No.: WO2006/006750

PCT Pub. Date: Jan. 19, 2006

(65) Prior Publication Data

US 2008/0050426 A1    Feb. 28, 2008

(30) Foreign Application Priority Data

Jul. 15, 2004  (KR) ................ 10-2004-0055088

(51) Int. Cl.
*A61K 36/258* (2006.01)
(52) U.S. Cl. ...................................................... 424/728
(58) Field of Classification Search .................. None
See application file for complete search history.

(56) References Cited

U.S. PATENT DOCUMENTS

| | | | | |
|---|---|---|---|---|
| 3,901,875 | A | * | 8/1975 | Park .............................. 536/5 |
| 4,684,628 | A | * | 8/1987 | Liu ................................ 514/26 |
| 2003/0031732 | A1 | * | 2/2003 | Kim et al. .................... 424/728 |

OTHER PUBLICATIONS

Derwent abstract of CN 1293033 A (2001).*
http://dictionary.reference.com/browse/wild—accessed May 2009.*

* cited by examiner

*Primary Examiner*—Susan C Hoffman
(74) *Attorney, Agent, or Firm*—Kirk Hahn

(57) ABSTRACT

The present invention relates to a method for preparing purified extract from wild ginseng showing anticancer activity such as inhibitory of cancer cell adherence, inhibitory of cancer cell metastasis and immunostimulating effect and a composition comprising the same prepared by inventive method. The composition have potent anticancer activity, therefore, it can be used as the therapeutics for treating and preventing various cancer diseases.

6 Claims, 2 Drawing Sheets

METHOD FOR PREPARING EXTRACT FROM WILD GINSENG SHOWING ANTICANCER ACTIVITY AND THE COMPOSITION COMPRISING THE SAME

This application is the U.S. National Phase under 35 U.S.C. §371 of International Application PCT Patent Application No. PCT/KR2004/001941, filed on Aug. 2, 2004, which claims priority to Korean Patent Application No. 10-2004-055088, filed on Jul. 15, 2004, the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

BACKGROUND OF THE INVENTION

1. Technical Field

The present invention relates to a method for preparing purified extract from wild ginseng showing anticancer activity and the composition comprising the same.

2. Background Art

Cancer is a malignant tumor occurred by the disorder in cell cycling resulting in abnormal differentiation and develops through three steps, i.e., initiation, promotion, and progression. The initiation of cancer can be occurred by sufficient amount of carcinogenic substance mostly, however, small amount of initiator gives rise to cell mutation, proliferates the number of mutated cells and finally the stimulation of tumor promoter causes to promote the differentiation of abnormal cells resulting in the formation of cancer tissue.

There have been numerous attempts or methods to develop a anticancer drug to treat cancer till now, for example, a method for screening a cytotoxic substance acting on cancer cell directly, a method for screening an modulating substance of the immunity of body, a method for screening an inhibiting substance of cancer cell metastasis, a method for screening an inhibiting substance of angiogenesis having been intensively studied recently, and so on.

Conventionally used anticancer drug may be classified into three groups: i.e., biological drugs such as gene or enzyme preparation, vaccine etc; chemotherapic agent (pure synthetic anticancer drug) such as taxol, vinblastine, etc; and natural product drug derived from natural resources. However, the biological drugs have not yet reached to be clinically used. Moreover, the chemotherapic agents have limit to use because of their various adverse actions such as the occurrence of intolerance to specific anticancer agent, a malfunction of bone marrow, stomach disorder such as vomiting, nausea, hair loss in spite of their potent anticancer activities (Gillman et al., *Maxwell Macmillan.*, 18, pp 1202, 1986; Chung et al., *J. Wonkwang Medical Sci.*, 3, pp 13-34, 1987). There have been reported that since most of anticancer drugs have low molecular weight of anticancer drug, the anticancer drug can permeate normal cell, especially actively differentiating cell, as well as cancer cell resulting in the damage in normal cell and it is easily excreted from urea, which requires relative amount of drug (Yamazaki et al., *Biosci. Biotech. Biochem.*, 56(1), pp 149, 1992; Tompson et al., *Exp. Cell Res.*, 41, pp 411-427, 1966; Ellem et al, *Devel. Biol.*, 118, pp 311-330, 1968).

Recently, there have been lots of attempts to develop anticancer agents having preventing or treating cancer diseases from crude drug or natural product.

Accordingly, there have been urgently needed to find effective substances providing with verified efficacy as well as low or at least toxicity from natural resource till now. Recently, alternative medicine, especially, Chinese medical therapy based on immune potentiating mechanism has been highlighted as an alternative method with conventional Western medicine to deviate the adverse effect of chemotherapy. Among the Chinese medical therapy, together with a use of plant extract extracted from Chinese drug showing immune potentiating activity and less toxicity, a use of acupuncture treatment with effective extract become highlighted in Korea, which comprises the steps consisting of: selecting plant or other natural resource having most effective activity on individual disease; extracting effective ingredient from the extract providing with maximized efficacy and minimized toxicity; inoculating or injecting the ingredient into the spots suitable for acupuncture or painful spots on the body and therefore it could endow with synergic effect due to the effect of acupuncture and the pharmacological effect of the ingredient. However, there have been needed to obtain more purified extract having less toxicity than crude form which could express its toxicity in administrating into injection or acupuncture such as fever, pain, edema etc.

There has been not reported or disclosed about a method for preparing purified extract from wild ginseng showing anticancer activity and the composition comprising the same in any of above cited literatures, the disclosures of which are incorporated herein by reference.

To investigate an effect of purified extract from wild ginseng prepared by the method of the present invention on the cancer and tumor cells, the inventors of the present invention have intensively carried out several In vitro and In vivo model experiments, and finally completed present invention by confirming that the purified extract shows anticancer activity and immunostimulating effect.

These and other objects of the present invention will become apparent from the detailed disclosure of the present invention provided hereinafter.

SUMMARY OF THE INVENTION

The present invention provides a method for preparing purified extract from wild ginseng having treating and preventing activity of cancer disease.

The present invention provides a pharmaceutical composition comprising a purified extract of wild ginseng prepared from above described method as an active ingredient in an effective amount to treat and prevent cancer disease by anticancer activity.

The present invention also provides a use of above extract for the preparation of pharmaceutical composition to treat and prevent cancer disease by anticancer activity in mammal or human.

DISCLOSURE OF THE INVENTION

Accordingly, it is an object of the present invention to provide a method for preparing a purified extract from wild ginseng comprising the steps consisting of; subjecting the wild ginseng material to distillation extracting method with extracting solvent repeatedly; freezing the distilled extract to obtain frozen purified extract; thawing the extract and filtrating to obtain purified extract.

It is an object of the present invention to provide a pharmaceutical composition comprising a purified extract of wild ginseng prepared by above described method as an active ingredient in an effective amount to treat and prevent cancer disease by anticancer activity.

It is an object of the present invention to provide a use of a purified extract of wild ginseng prepared by above described method for the preparation of therapeutic agent for the treatment and prevention of cancer disease by anticancer activity in mammal or human.

It is an object of the present invention to provide a method of treating or preventing cancer disease by anticancer activity in mammal or human comprising administering to said mammal or human an effective amount of a purified extract of wild ginseng prepared by above described method, together with a pharmaceutically acceptable carrier thereof.

The term disclosed herein "extracting solvent" comprises water, lower alcohols such as methanol, ethanol, preferably water.

The term disclosed herein "wild ginseng material" comprises all the wild ginseng cultivated or naturally grown wild ginseng in the world, for example, Korea, Japan, Russia, China, Europe, America etc.

The pharmaceutical composition of the present invention can contain about 0.01~50% by weight of the above extract based on the total weight of the composition.

An inventive a purified extract of wild ginseng may be prepared in accordance with the following preferred embodiment.

Hereinafter, the present invention is described in detail.

An inventive purified extract of wild ginseng can be prepared in detail by following procedures, The inventive purified extract of wild ginseng can be prepared by follows;

Specifically, it is an object of the present invention to provide a method for preparing a purified extract from wild ginseng comprising the steps consisting of; subjecting the wild ginseng material to $1^{st}$ distillation extracting method with extracting solvent to obtain $1^{st}$ distillate at $1^{st}$ step; subjecting the $1^{st}$ distillate to $2^{nd}$ distillation extracting method with extracting solvent to obtain $2^{nd}$ distillate at $2^{nd}$ step; freezing the $2^{nd}$ distillate to obtain frozen purified extract at $3^{rd}$ step; thawing the extract and filtrating to obtain filtrated extract at $4^{th}$ step; heating the filtrate with double boiler and refreezing at $5^{th}$ step; thawing and sterilizing the extract to obtain the purified extract of the present invention at $6^{th}$ step.

Specifically, At $1^{st}$ step, it is preferable that the wild ginseng material is poured to polar solvent selected from water, lower alcohol such as methanol, ethanol, propanol and the solvent mixture thereof preferably, water, more preferably, water in the ratio ranging from 1.0 kg to 3.0 kg of material per liter of water and left alone at room temperature for the period ranging from 1 to 4 hours, preferably, 3 hours. Subsequently, it is heated with distillation apparatus at the temperature ranging from 60 to 120° C., preferably 80 to 100° C., more preferably, 100° C., for the period ranging from 6 to 24 hours, preferably, from 8 to 10 hours gradually to obtain $1^{st}$ distillate.

At $2^{nd}$ step, it is preferable that the $1^{st}$ distillate is added to the boiling chip containing flask equipped with distillation apparatus and heated at the temperature ranging from 60 to 120° C., preferably 80 to 100° C., more preferably, 100° C., for the period ranging from 7 to 24 hours, preferably, from 8 to 12 hours gradually and the heating process is maintained to the extent that the volume of concentrate is reduced to be in the ranging 70 to 90 (v/v) % to obtain $2^{nd}$ distillate.

At $3^{rd}$ step, it is preferable that the $2^{nd}$ distillate is subjected to freezing process at the temperature ranging from −5 to −15° C., preferably from −8 to −12° C. and the process is maintained to the extent that the volume of un-frozen fraction is decreased to be less than 5% of the total volume. The un-frozen fraction is removed and the remaining distillate is subjecting to thawing process. Those freezing and removing un-frozen fraction processes can be repeated, preferably 3 to 6 times, to obtain frozen purified extract of the present invention. Through $3^{rd}$ step, toxic substance in wild ginseng material at $1^{st}$ step is almost or completely removed in purified extract prepared by this step.

At $4^{th}$ step, it is preferable that the frozen purified extract at $3^{rd}$ step is subjected to thawing process at room temperature and filtrating process is followed with filter paper having pore size ranging from 0.1 to 0.6 μm, preferably to 0.4 μm to obtain filtrates.

At $5^{th}$ step, the filtrate prepared in above step is heated with double boiler at the temperature ranging from 60 to 120° C., preferably 80 to 100° C., more preferably, 100° C., in the period ranging from 20 to 40 mins, preferably, 30 mins, and is refrozen completely at the temperature ranging from −30 to −10° C., preferably, at −15° C. to obtain frozen purified extract.

At $6^{th}$ step, the frozen filtrate is thawed and sterilized to obtain final purified extract of the present invention.

In above described the $1^{st}$ step, the concentration of the $1^{st}$ distillate can be controlled by changing the ratio of material pursuant to the purpose of the present invention.

In above described purification process, the extract can be separated into two parts, i.e., frozen part and unfrozen part according to the difference with specific ingredients. Since the ingredients having stronger toxicity being contained in the extract become frozen slower than that having weaker toxicity because of the low freezing point, the unfrozen part containing most of toxic ingredient can be removed by repeating the above freezing processes, Accordingly, it is an object of the present invention to provide a pharmaceutical composition comprising a purified extract of wild ginseng prepared by above described method as an active ingredient in an effective amount to treat and prevent cancer disease by anticancer activity.

It is an object of the present invention to provide a use of a purified extract of wild ginseng prepared by above described method for the preparation of therapeutic agent for the treatment and prevention of cancer disease by anticancer activity in human or mammal.

It is an object of the present invention to provide a method of treating or preventing degenerative brain disease by protecting neuronal cell in a mammal or human comprising administering to said mammal or human an effective amount of a purified extract of wild ginseng prepared by above described method, together with a pharmaceutically acceptable carrier thereof.

Through the in vitro and in vivo model experiments to confirm the effect of the purified extract of the present invention on the cancer and tumor cells, present inventors confirm that the purified extract shows anticancer activity and immunostimulating effect.

Therefore, the purified extract of the present invention can be useful in treating and preventing cancer disease.

In addition to the efficacy, the purified extract of the present invention can be used safely in long-term administration since it has been used as a commercial crude drug since long years ago.

The inventive composition for treating and preventing cancer disease may comprises above extracts as 0.01~50% by weight based on the total weight of the composition.

The inventive composition may additionally comprise conventional carrier, adjuvants or diluents in accordance with a using method well known in the art. It is preferable that said carrier is used as appropriate substance according to the usage and application method, but it is not limited. Appropriate diluents are listed in the written text of Remington's Pharmaceutical Science (Mack Publishing co, Easton Pa.).

Hereinafter, the following formulation methods and excipients are merely exemplary and in no way limit the invention.

The composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents that are commonly used to produce an injection. Suitable examples of the carriers include physiological saline, polyethylene glycol, ethanol, vegetable oils, isopropyl myristate, etc., but are not limited to them. For topical administration, the extract of the present invention can be formulated in the form of ointments and creams.

Pharmaceutical formulations containing present composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), injectable preparation (solution, suspension, emulsion) or acupuncture injectable preparation.

The composition of the present invention in pharmaceutical dosage forms may be used in the form of their pharmaceutically acceptable salts, and also may be used alone or in appropriate association, as well as in combination with other pharmaceutically active compounds.

The desirable dose of the inventive extract or composition varies depending on the condition and the weight of the subject, severity, drug form, route and period of administration, and may be chosen by those skilled in the art. However, in order to obtain desirable effects, it is generally recommended to administer at the amount ranging 10 g/kg, preferably, 1 to 3 g/kg by weight/day of the inventive extract or compounds of the present invention. The dose may be administered in single or divided into several times per day. In terms of composition, the amount of inventive extract should be present between 0.01 to 50% by weight, preferably 0.5 to 40% by weight based on the total weight of the composition.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection or acupuncture injection onto the spots suitable for acupuncture.

Inventive extract of the present invention have no toxicity and adverse effect therefore; they can be used with safe.

It will be apparent to those skilled in the art that various modifications and variations can be made in the compositions, use and preparations of the present invention without departing from the spirit or scope of the invention.

BRIEF DESCRIPTION OF THE DRAWINGS

The above and other objects, features and other advantages of the present invention will more clearly understood from the following detailed description taken in conjunction with the accompanying drawings, in which.

BEST MODE FOR CARRYING OUT THE INVENTION

Figure 1:
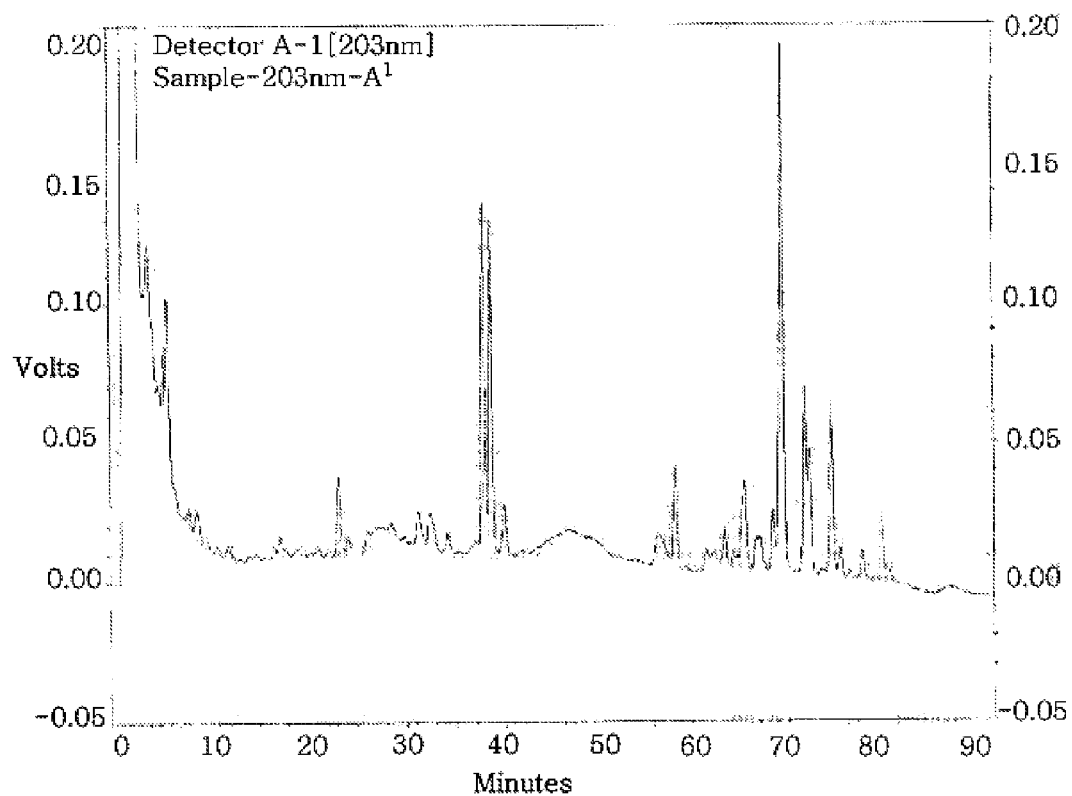
FIG. 1 shows HPLC analyzing unpurified extract of naturally grown wild ginseng.

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

EXAMPLES

The following Reference Example, Examples and Experimental Examples are intended to further illustrate the present invention without limiting its scope.

Comparative Example 1

Preparation of not Purified Extract of Naturally Grown Wild Ginseng 2.5 kg of Sanyang wild ginseng originated from naturally grown wild ginseng was washed with salt water and sliced into piece at the width of 3 mm, poured into flask containing 1 liter of water and heated at 100° C. for eight. The distillate was filtered with filter paper having a pore size ranging from 0.1 to 0.6 μm. The filtrate was cooled at room temperature, sterilized and stored in sterilized bottle maintaining the temperature at below 4° C. to use as a sample in following experiments.

Comparative Example 2

Preparation of not Purified Extract of Cultivated Wild Ginseng 2 kg of cultivated wild ginseng originated from naturally grown wild ginseng was washed with salt water and sliced into piece at the width of 3 mm, poured into flask containing 1 liter of water and heated at 100° C. for eight. The distillate was filtered with filter paper having a pore size ranging from 0.1 to 0.6 μm. The filtrate was cooled at room temperature, sterilized and stored in sterilized bottle maintaining the temperature at below 4° C. to use as a sample in following experiments.

Example 1

Preparation of the Purified Extract of Naturally Grown Wild Ginseng 2.5 kg of Sanyang wild ginseng originated from naturally grown wild ginseng was washed with salt water and sliced into piece at the width of 3 mm, poured into flask containing 1 liter of water and left alone for three hours at 20° C.

The flask was equipped with distillation apparatus and heated at 100° C. for eight hours to obtain $1^{st}$ distillate. 5 g of boiling chip and the $1^{st}$ distillate were poured flask equipped with distillation apparatus and the flask was further heated at 100° C. for ten hours to obtain $2^{nd}$ distillate. The $2^{nd}$ distillate was frozen to the extent that the volume of unfrozen part become less than 5% of total volume at −10° C. and the unfrozen part was discarded. Remaining frozen part was thawed at room temperature. Above freezing and thawing steps were further repeated two times. After the frozen part was thawed, it was filtered with filter paper having a pore size of 0.1~0.6 μm and the filtrate was heated in double boiler at 90° C. for 30 mins. The filtrate was cooled and frozen completely at −15° C. The frozen purified extract was thawed at room temperature, sterilized and stored in sterilized bottle maintaining the temperature at below 4° C. to use as a sample in following experiments.

Example 2

Preparation of the Purified Extract of Cultivated Wild Ginseng 2 kg of cultivated wild ginseng supplied with Kyunghee University (Seoul, Korea) was washed with salt water and sliced into piece at the width of 3 mm, poured into flask containing 1 liter of water and left alone for three hours at 20° C.

Further steps were performed with the methods similar to those in Example 1 to obtain purified extract of cultivated wild ginseng and it was used as a sample in following experiments.

Example 3

Content Analysis of Above Comparative Example 1 and Example 1

The content of saponin in above Comparative Example 1 and Example 1 was determined by using High Performance Liquid chromatography (column: Phenomenex Nuna C18 (5 μm, 150×2.0 mm), flow rate: 0.3 ml/min, detector: UV detector 203 nm, developing solvent: starting solvent; $CH_3CN$:$H_2O$=15:85 and from 0% to 30% in $CH_3CH$:$H_2O$=80:20 more than 70 minutes, room temperature).

Figure 2:
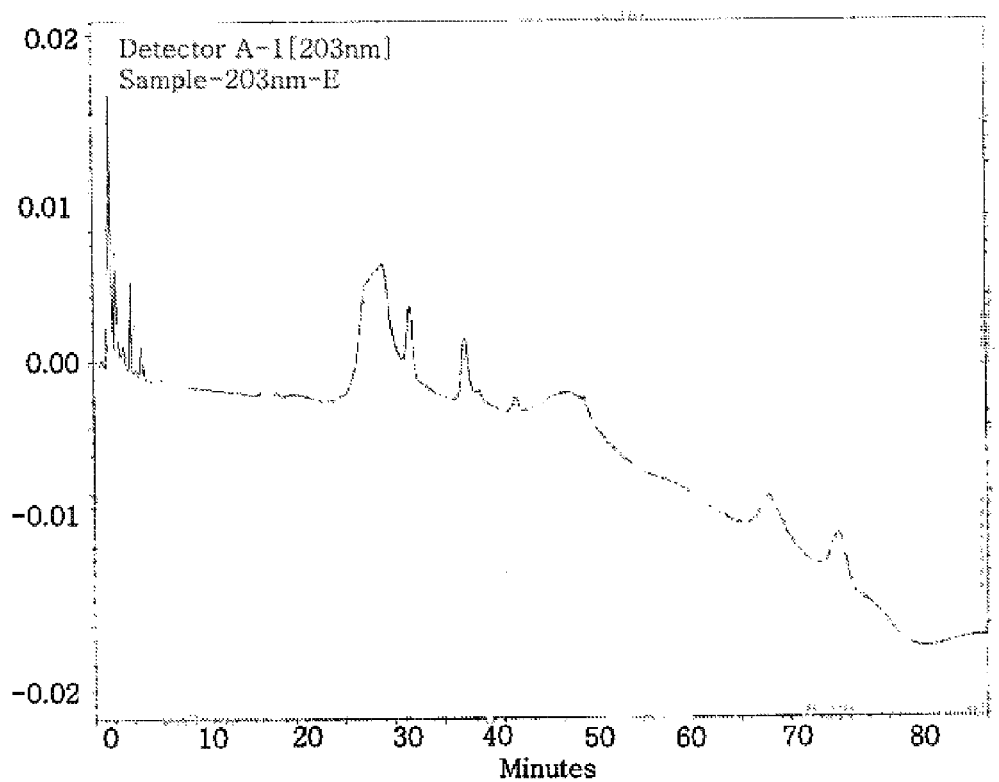
FIG. 2 shows HPLC analyzing the purified extract of naturally grown wild ginseng.

As shown in FIG. 1 and FIG. 2, the result of above content analysis was detected that the content of saponin in above Comparative Example 1 and Example 1 was a remarkable difference between the two.

Reference Example 1

Cell Culture

U937 cells (human leukemia cell line), A549 cells (human lung cancer cell line) and MDA-MB-231 (human breast cancer cell line) cells were grown on the culture dish having 100 mm diameter (TPP Co., Ltd., Switzerland) in RPMI1640 (Gibco BRL Co., Ltd., USA), supplemented with 10% fetal bovine serum which was inactivated at 37° C. in 5% $CO_2$ and 95% air condition in a humidified incubator.

Experimental Example 1

Cell Cytotoxicity Determination

The cell cytotoxicity of wild ginseng in U937 cell (human leukemia cell line), A549 cell (human lung cancer cell line) and MDA-MB-231 (human breast cancer cell line) was determined by (3-[4,5-dimethylthiazol-2-yl]-2,5-diphenyl tetrazolium bromide (MTT) assay method.

Cells on 10 mm culture dish were treated with 500 μl of trypsin-EDTA (Gibco BRL Co., Ltd., U.S.A.) to separate from the dish and 10 ml of fresh medium was added thereto so as to neutralize trypsin-EDTA solution and obtain cell suspension.

$1 \times 10^4$ cells/well were seeded in 96-well plate and after 24 hours incubation. The cells were treated with 100 μl/well of various concentrations of the extracts prepared in Comparative Example 1, 2 and Example 1, 2, i.e., 0, 125, 250, 500 and 1000 μg/ml respectively, and incubated for another 48 hours. After 48 hours, the medium was discarded and 10 μl of MTT solution (5 mg/ml suspended in medium, Sigma Co., U.S.A.) diluted with PBS buffer adjusted the concentration to 5 mg/ml was added to each cells to incubate at 37° C. for 4 hours. The medium was washed with PBS to remove remaining MTT reagent and 100 μl of DMSO (Dimethyl Sulfoxide) was dropped into each well. The plate was incubated for 20 minutes at room temperature and then UV absorbance the samples was measured by microplate reader (ELISA reader, DENLEY Co., Japan) to calculate the cell viability at 570 nm.

The cell viability rate of negative control group treated with only medium was calculated as a 100% and those of other sample and positive control were calculated.

As a positive control group, 100 ul/well of various concentrations of adriamycin, i.e., 0, 3.125, 6.25, 12.5, 25 were seeded onto 96 well plates, incubated for 48 hours and treated with diluted MTT in the concentration of 5 mg/ml.

The measured absorbance showing the reduced amount of existing cellular enzyme in MTT was proportioned to survival cell density. The concentration of sample required to inhibit the survival of cancer cell by 50% was expressed $IC_{50}$ values.

At the result, Comparative Example 1, 2 and Example 1, 2 treatment groups ($IC_{50}$, >300 μl/ml) showed low cytotoxic effects while adriamycin treatment group showed relatively strong cytotoxic effects ($IC_{50}$, 3 μg/ml) on U937, A5497 and MDA-MB-231 cancer cells (See Table 1, 2 and 3).

TABLE 1

| Cytotoxicity on U937 cells | |
|---|---|
| Sample | $IC_{50}$ (μl/ml) |
| Comparative Example 1 | >300 |
| Example 1 | >300 |
| Comparative Example 2 | >300 |
| Example 2 | >300 |
| Adriamycin | 3 |

TABLE 2

Cytotoxicity on A549 cells

| Sample | IC$_{50}$ (μl/ml) |
|---|---|
| Comparative Example 1 | >300 |
| Example 1 | >300 |
| Comparative Example 2 | >300 |
| Example 2 | >300 |
| Adriamycin | 3 |

TABLE 3

Cytotoxicity on MDA-MB-231 cells

| Sample | IC$_{50}$ (μl/ml) |
|---|---|
| Comparative Example 1 | >300 |
| Example 1 | >300 |
| Comparative Example 2 | >300 |
| Example 2 | >300 |
| Adriamycin | 3 |

Experimental Example 2

Inhibition of Cancer Cell for Adhering to Cytoplasm

If cancer cells moves from first occurring area to other organ, the cancer cell need cell adhering ability to specific substance in the cytoplasm i.e., collagen, laminin, gelatin, etc., or blood endothelium for metastasis.

To determine the inhibitory effect of cell adhering ability of the extract of the present invention, MDA-MB-231 cells ($1 \times 10^6$ cells/well) were seeded in 96 well plate coated by 0.1% gelatin and various concentrations of Comparative Example 1, 2 and Example 1, 2 (0, 62.5, 125, 250 and 500 μg/ml) were treated thereto to the concentration of 100 μl/well respectively. The cells were incubated till the cells was attached to bottom of plate at 37° C. incubator and the plate was washed with PBS buffer cautiously. The attached cells were stained with crystal violet staining agent and the values of OD were measured by microplate reader (ELISA reader, DENLEY Co., Japan) at 620 nm.

At the result, it is confirmed that Comparative Example 1, 2 and Example 1, 2 treatment groups showed that they inhibited the adhesion of MDA-MB-231 cells to gelatin in dose dependent manner (See Table 4).

TABLE 4

| Sample | Concentration (μl/ml) | Inhibition of adhesion (%) |
|---|---|---|
| Comparative Example 1 | 62.5 | 13.32 ± 2.31 |
| | 125 | 17.21 ± 4.38 |
| | 250 | 20.94 ± 2.06 |
| | 500 | 34.84 ± 1.04 |
| Example 1 | 62.5 | 15.18 ± 0.74 |
| | 125 | 19.81 ± 2.17 |
| | 250 | 21.32 ± 3.33 |
| | 500 | 38.37 ± 5.43 |
| Comparative Example 2 | 62.5 | 15.04 ± 3.22 |
| | 125 | 18.90 ± 3.31 |
| | 250 | 20.46 ± 4.46 |
| | 500 | 25.91 ± 6.30 |
| Example 2 | 62.5 | 15.54 ± 1.92 |
| | 125 | 19.56 ± 3.31 |
| | 250 | 22.32 ± 2.91 |
| | 500 | 30.26 ± 3.30 |

Experimental Example 3

Inhibitory Effect on the Metastasis of MDA-MB-231 Cell

To determine the inhibitory effect of the extract of the present invention on cancer cell metastasis, Polycarbonate membrane having a pore size of 8 μm was sufficiently coated with 50 μg of matrigel for 1 hour and dried in the air for 24 hours. Each 30 μl of conditioned media supplemented with 0.1% BSA was poured onto lower compartment of Boyden chamber. 50 μl of MDA-MB-231 cells ($1 \times 10^6$ cells/well) supplemented with RPMI1640 (FBS-free) media containing 0.1% BSA treated with 50 μl of extract prepared by Comparative Example 1, 2 and Example 1, 2 were poured onto upper compartment of Boyden chamber, respectively. After incubating for 16 hours at 37° C. in 5% CO$_2$ and 95% air condition in a humidified incubator, the membrane was fixed by MeOH and stained with Quic solution (Diffco Co. Ltd). The numbers of cells invaded from upper compartment to lower compartment were counted by optical spectroscopy.

At the result, it was confirmed that the groups treated with the extract of Example 1 and 2 showed stronger inhibition of the metastasis of MDA-MB-231 cells in dose dependent manner compared with the groups treated with the extract of Comparative Example 1 and 2 (See Table 5).

TABLE 5

| Sample | Concentration (μl/ml) | Inhibition rate (%) |
|---|---|---|
| Comparative Example 1 | 62.5 | 36.43 ± 3.08 |
| | 125 | 49.49 ± 5.85 |
| | 250 | 50.06 ± 1.69 |
| | 500 | 69.54 ± 5.35 |
| Example 1 | 62.5 | 39.54 ± 4.85 |
| | 125 | 52.94 ± 3.12 |
| | 250 | 58.02 ± 3.59 |
| | 500 | 77.75 ± 6.54 |
| Comparative Example 2 | 62.5 | 14.11 ± 2.85 |
| | 125 | 38.48 ± 4.22 |
| | 250 | 46.67 ± 5.27 |
| | 500 | 48.05 ± 2.15 |
| Example 2 | 62.5 | 38.32 ± 3.86 |
| | 125 | 42.22 ± 3.05 |
| | 250 | 47.36 ± 3.94 |
| | 500 | 50.69 ± 4.21 |

Experimental Example 4

Inhibitory Effect on the Volumetric Increase of Cancer Cell Using by Lewis Lung Carcinoma Cell To determine the inhibitory effect on the volumetric increase of cancer cell, following experiment was performed by modifying the procedure disclosed in the literature (Teruhiro et al., *Cancer Res.*, 56, pp 2809-14, 1996).

Lewis lung carcinoma cells ($1 \times 10^6$ cells/well) which had been sub-cultured in vivo of experimental mouse and adjusted the concentration to $1 \times 10^6$ cells/well, was injected into the left armpit of BDF-1 male mice (6-week-old). After 24 hours, adriamycin in the concentration of 0.5 and 1 mg/mouse, and the extracts prepared in Comparative Example 1, 2 and Example 1, 2 in the concentration of 50 and 100 μl/mouse were injected into the mice intraperitoneally. The injection of samples was maintained for 2 weeks until the tumor volume of non-treatment group used as control group become to 2 cm$^3$. After 2 weeks, the tumor volume was calculated by using following mathematical formulae 1 and 2 to measure the inhibition rate of tumor volume.

$$\text{Tumor volume}(cm^3) = \frac{L \times w^2}{2} \quad \text{[Mathematical formulae 1]}$$

L (cm): Length of the tumor $W^2$ ($cm^2$): Width of the tumor $$\text{Inhibition of tumor volume}(\%) = \frac{A - B}{A} \times 100 \quad \text{[Mathematical formulae 2]}$$

A: Tumor volume ($cm^3$) of control group

B: Tumor volume ($cm^3$) of sample treatment group

At the result, it was confirmed that the groups treated with the extract of Example 1 and 2 showed stronger inhibition of the volumetric growth of Lewis lung carcinoma cells in dose dependent manner compared with the groups treated with the extract of Comparative Example 1 and 2 (See Table 6).

TABLE 6

| Sample | Concentration (μl/mouse) | Inhibition effect (%) |
|---|---|---|
| Comparative Example 1 | 50 | 30.05 ± 9.47 |
|  | 100 | 48.95 ± 2.87 |
| Example 1 | 50 | 75.94 ± 10.70 |
|  | 100 | 90.12 ± 11.25 |
| Comparative Example 2 | 50 | 29.04 ± 10.94 |
|  | 100 | 40.38 ± 13.32 |
| Example 2 | 50 | 73.05 ± 11.37 |
|  | 100 | 88.94 ± 10.83 |
| adriamycin | 0.5 mg | 31.20 ± 8.05 |

Experimental Example 5

Body Weight Measurement

The body weight of mice prepared in above Experimental Example 4 was measured with automatic weight measurement equipment (Jenix, Dongsintonsang, Korea) during the experimental period.

At the result, Example 1 and 2 treatment groups showed significant increase of the body weight while most of conventionally available anticancer drugs showed the decrease of the body weight because of their adverse action.

Experimental Example 6

Inhibitory Effect on the Metastasis of B16-F10 Melanoma Cell

To determine the inhibitory effect on the metastasis of cancer cell, B16-F10 melanoma cells ($2.5 \times 10^5$ cells/well) was injected into lateral tail vein of C57BL/6 mice. After 24 hours, the extracts prepared in Comparative Example 1, 2 and Example 1, 2 in the concentration of 100 μl/mouse/day were injected, respectively. After 14 days of the injection, above experimental mice was killed and the colony of lung metastatic tumor cell delivered from the mouse was observed by macrography.

At the result, it was confirmed that the extract prepared in Example 1 and 2 showed stronger inhibitory effect on the metastasis of B16-F10 melanoma cells compared with the extracts prepared in Comparative Example 1 and 2 (See Table 7).

TABLE 7

| Sample | Colony number | Inhibition rate (%) |
|---|---|---|
| Comparative Example 1 | 47.02 ± 13.83 | 42 |
| Example 1 | 33.96 ± 10.48 | 58 |
| Comparative Example 2 | 65.51 ± 11.32 | 18 |
| Example 2 | 52.23 ± 18.46 | 35 |
| Non-treatment | 80.4 ± 17.81 | 0 |

Experimental Example 7

Immunostimulating Effect Using by Splenic Leucocytes of BALB.c Mouse

To determine the immunostimulating effect of the extract of the present invention, splenic leucocytes ($1 \times 10^6$ cells/ml) of BALB c mouse were suspended in RPMI1640 medium (Gibco BRL Co., Ltd., USA) supplemented with 100 μg/ml of streptomycin, 100 U/ml of penicillin and 10% fetal bovine serum, and treated with 200 μl/ml of the extracts of Comparative Example 1, 2 and Example 1, 2, respectively. The solution was incubated at 37° C. in 5% $CO_2$ and 95% air condition in a humidified incubator for 3 days and the formation of leucocytes was determined by Flow cytometry. 200 μg/ml of adriamycin treatment group was used as control group.

At the result, it was confirmed that while the adriamycin treatment group decreased the immunity by 26.1%, the Example 1 and 2 treatment groups showed higher increased synthesis rate of lymphocytes compared with Comparative Example 1 and 2 treatment groups (See Table 8).

TABLE 8

| Sample | Concentration (μg/ml) | Increase rate of lymphocyte (%) |
|---|---|---|
| Adriamycin | 200 | −21.6 |
| Comparative Example 1 | 200 | 30.6 |
| Example 1 | 200 | 57.2 |
| Comparative Example 2 | 200 | 32.1 |
| Example 2 | 200 | 54.3 |

Experimental Example 8

Toxicity Test

Methods (1)

The acute toxicity tests on ICR mice (mean body weight 25±5 g) and Sprague-Dawley rats (235±10 g, Jung-Ang Lab Animal Inc.) were performed using the extract of the Example 1. Four group consisting of 10 mice or rats was administrated orally intraperitoneally with 250 mg/kg, 500 mg/kg, 1000 mg/kg and 5000 mg/kg of test sample or solvents (0.2 ml, i.p.) respectively and observed for 2 weeks.

Methods (2)

The acute toxicity tests on ICR mice and Sprague-Dawley rats were performed using the extract of the Example 2. Four group consisting of 10 mice or rats was administrated intraperitoneally with 25 mg/kg, 250 mg/kg, 500 mg/kg and 725 mg/kg of test sample or solvents (0.2 ml, i.p.), respectively and observed for 24 hours.

Results

There were no treatment-related effects on mortality, clinical signs, body weight changes and gross findings in any group or either gender. These results suggested that the extract prepared in the present invention were potent and safe.

Hereinafter, the formulating methods and kinds of excipients will be described, but the present invention is not limited to them. The representative preparation examples were described as follows.

| Preparation of powder | |
|---|---|
| Dried powder of Example 1 | 50 mg |
| Lactose | 100 mg |
| Talc | 10 mg |

Powder preparation was prepared by mixing above components and filling sealed package.

| Preparation of tablet | |
|---|---|
| Dried powder of Example 1 | 50 mg |
| Corn Starch | 100 mg |
| Lactose | 100 mg |
| Magnesium Stearate | 2 mg |

Tablet preparation was prepared by mixing above components and entabletting.

| Preparation of capsule | |
|---|---|
| Dried powder of Example 1 | 50 mg |
| Corn starch | 100 mg |
| Lactose | 100 mg |
| Magnesium Stearate | 2 mg |

Tablet preparation was prepared by mixing above components and filling gelatin capsule by conventional gelatin preparation method.

| Preparation of injection | |
|---|---|
| Dried powder of Example 2 | 50 mg |
| Distilled water for injection | optimum amount |
| PH controller | optimum amount |

Injection preparation was prepared by dissolving active component, controlling pH to about 7.5 and then filling all the components in 2 ml ample and sterilizing by conventional injection preparation method.

| Preparation of liquid | |
|---|---|
| Dried powder of Example 2 | 0.1~80 g |
| Sugar | 5~10 g |
| Citric acid | 0.05~0.3% |
| Caramel | 0.005~0.02% |
| Vitamin C | 0.1~1% |
| Distilled water | 79~94% |
| $CO_2$ gas | 0.5~0.82% |

Liquid preparation was prepared by dissolving active component, filling all the components and sterilizing by conventional liquid preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, the purified extracts of wild ginseng prepared by inventive method have potent anticancer activity such as inhibitory of cancer cell adherence, inhibitory of cancer cell metastasis and immunostimulating effect, therefore, it can be used as the therapeutics for treating and preventing various cancer diseases.

What is claimed is:

1. A method for preparing a purified extract from wild ginseng comprising the steps of; subjecting a wild ginseng material to $1^{st}$ distillation extracting method with water to obtain $1^{st}$ distillate at $1^{st}$ step; subjecting the $1^{st}$ distillate to $2^{nd}$ distillation extracting method with water to obtain $2^{nd}$ distillate at $2^{nd}$ step; freezing the $2^{nd}$ distillate to obtain frozen purified extract at $3^{rd}$ step; thawing the frozen purified extract and filtering to obtain a filtrate of extract at $4^{th}$ step; heating the filtrate with double boiler and refreezing at $5^{th}$ step; thawing and sterilizing the extract to obtain a purified extract at $6^{th}$ step.

2. The method of claim 1, wherein said $1^{st}$ step comprises pouring water on said material in the ratio ranging from 1.0 kg to 3.0 kg of material per liter of water; standing at room temperature for a period ranging from 1 to 4 hours; subsequently, heating with distillation apparatus at below 100° C. for a period ranging from 6 to 24 hours to obtain $1^{st}$ distillate.

3. The method of claim 1, wherein said $2^{nd}$ step comprises: adding boiling chip containing flask equipped with distillation apparatus to $1^{st}$ distillate; heating at 100° C., for a period ranging from 7 to 24 hours gradually to the extent that the volume of $1^{st}$ distillate is reduced to a range of 70% to 90% (v/v) to obtain $2^{nd}$ distillate.

4. The method of claim 1, wherein said $3^{rd}$ step comprises: freezing $2^{nd}$ distillate at a temperature ranging from −5 to −15° C. to the extent that the volume of un-frozen fraction is decreased to be less than 5% of the total volume; removing the un-frozen fraction; thawing remaining distillate; repeating freezing and removing un-frozen fraction processes at 3 to 6 times to obtain frozen purified extract.

5. The method of claim 1, wherein said $4^{th}$ step comprises: thawing the frozen purified extract at $3^{rd}$ step at room temperature; and filtering with filter paper having pore size ranging from 0.1 to 0.6 μm to obtain a filtrate.

6. The method of claim 1, wherein said $5^{th}$ step comprises: heating with double boiler at 100° C. for a period ranging from 20 to 40 minutes; and refreezing to obtain frozen purified extract.

* * * * *